(12) United States Patent
Alley

(10) Patent No.: US 7,029,627 B2
(45) Date of Patent: Apr. 18, 2006

(54) APPARATUS FOR SAMPLING, STORING, PRESERVING AND TESTING A SPECIMEN

(76) Inventor: Kenneth A. Alley, 311 Foundryville, Berwick, PA (US) 18603

( * ) Notice: Subject to any disclaimer, the term of this patent is extended or adjusted under 35 U.S.C. 154(b) by 439 days.

(21) Appl. No.: 10/267,059

(22) Filed: Oct. 7, 2002

(65) Prior Publication Data

US 2003/0190259 A1  Oct. 9, 2003

Related U.S. Application Data

(60) Provisional application No. 60/327,227, filed on Oct. 5, 2001.

(51) Int. Cl.
*G01N 31/00* (2006.01)
(52) U.S. Cl. ............ 422/58; 422/50; 422/55; 422/56; 422/57; 422/59; 422/61; 422/68.1; 422/82.05; 422/99; 422/100; 422/101; 422/102; 422/104
(58) Field of Classification Search ............ 422/50, 422/55, 56, 57, 58, 59, 61, 68.1, 82.05, 99, 422/100, 101, 102, 104
See application file for complete search history.

(56) References Cited

U.S. PATENT DOCUMENTS

| | | | |
|---|---|---|---|
| 3,774,455 A | 11/1973 | Seidler et al. | 73/444 |
| 4,709,705 A | 12/1987 | Truglio | 128/750 |
| 4,927,605 A * | 5/1990 | Dorn et al. | 422/102 |
| 4,979,402 A | 12/1990 | Ryan et al. | 73/864.64 |
| 5,268,148 A | 12/1993 | Seymour | 422/101 |
| 5,393,496 A | 2/1995 | Seymour | 422/101 |
| 5,494,646 A | 2/1996 | Seymour | 422/101 |
| 5,709,838 A | 1/1998 | Porter et al. | 422/61 |
| 5,910,122 A | 6/1999 | D'Angelo | 600/573 |
| 5,998,214 A | 12/1999 | Guirguis | 436/165 |

(Continued)

OTHER PUBLICATIONS

Copy of brochure for Drug Check screening device; Drug Free Enterprises, Inc.; Scotts Valley, CA (2 pgs.).

(Continued)

*Primary Examiner*—Jill Warden
*Assistant Examiner*—Sam P. Siefke
(74) *Attorney, Agent, or Firm*—Law Office of Mark Garzia; Mark A. Garzia (57) ABSTRACT

A multiple-chamber container for sampling, storing and preserving for later testing a sample. A swab having a foam tip is used to collect a sample (the sample must have some liquid component, e.g., saliva, urine, blood, etc.). After the foam tip is used to collect a specimen, the swab is inserted into the container where the foam tip is compressed and a portion of the specimen that was sampled is diverted into each chamber. The swab is locked into the container thereby sealing the specimen inside. At least one test strip is positioned inside one of the chambers to test the sample. The sample in the other chamber(s) are separated and can be stored for a period of time. A preservative may be used to help keep the specimen during storage.

19 Claims, 5 Drawing Sheets

U.S. PATENT DOCUMENTS

| | | | |
|---|---|---|---|
| 6,074,606 A | 6/2000 | Sayles | 422/58 |
| 6,294,710 B1 | 9/2001 | Schmidt et al. | 604/378 |
| 6,537,496 B1 | 3/2003 | Knappe et al. | 422/58 |
| 6,669,908 B1* | 12/2003 | Weyker et al. | 422/58 |
| 6,786,106 B1* | 9/2004 | Alley | 73/864.51 |
| 2002/0048819 A1* | 4/2002 | Alley | 436/169 |
| 2003/0064526 A1* | 4/2003 | Niedbala et al. | 436/165 |
| 2004/0228767 A1* | 11/2004 | Alley | 422/68.1 |

OTHER PUBLICATIONS

Copy from website for Drug Check screening device; Drug Free Enterprises, Inc.; www.drugcheck.com (2 pgs.).

Copies of 3 brochures from Phamatech, Inc.; San Diego, CA; including Pregnancy and Ovulation brochure (2 pgs.); QuickScreen brochure (1 pg.); and ClearChoice brochure (2 pgs.).

* cited by examiner

APPARATUS FOR SAMPLING, STORING, PRESERVING AND TESTING A SPECIMEN

CROSS-REFERENCE TO RELATED APPLICATION

The present application claims the benefit under any applicable U.S. statute to U.S. Provisional Application No. 60/327,227 filed Oct. 5, 2001, titled APPARATUS FOR SAMPLING, STORING AND TESTING A SPECIMEN.

This application incorporates by reference U.S. Provisional Appln. No. 60/327,227, as if fully set forth herein.

FIELD OF THE INVENTION

The present invention relates generally to a drug screening apparatus and, more specifically, to a self-contained, tamper-proof system for testing, storing and screening for drugs and drug metabolites. The invention is not limited to screening for drugs.

BRIEF DESCRIPTION OF THE PRIOR ART

More businesses are requiring new employees to undergo pre-employment drug testing before hiring. Also, post-accident drug testing is almost routine, especially when flammable or hazardous waste hauling is involved, or where the safety of a large number of people are concerned (e.g., oil tanker captain, truck driver or high-speed train engineer). A saliva sample may be obtained and sent to a lab for testing. In most cases the sample will degrade within a short period of time unless the sample is treated. There are companies that offer a device to store and transfer the saliva sample until a lab can perform specific test. There are also saliva test available to perform rapid test, thus providing immediate results. If the test turns up positive, the specimen must then be sent to a more sophisticated, usually remotely located, testing lab. Unfortunately, the specimen will not provide accurate results if too much time passes. This alone, is one reason that a urine sample is often the preferred method for testing for Drugs and Drug Metabolites. There are companies that developed preservatives that may be used to store and preserve salvia samples. Such devices provide a swab to collect a sample and a container, which is pre-filled with a preservative that is used to treat and store the sample during shipment to a lab where the sample will then be tested.

SUMMARY OF THE INVENTION

The present invention is a self-contained, tamper-proof screening, testing and storage apparatus. The present invention also splits the sample and if desired, the untested portion of the sample may be treated, thus preserving the sample for future testing. The present invention consists of a divided container, wherein one side of the container holds rapid test strips and the other side may hold a preservative (if desired), a bottom plug that snaps and locks onto the bottom end of the container, a top cover that snaps and locks onto the top end of the container, a stopper that seals the container prior to use and a sampling swab that collects the sample and eventually seals and activates the apparatus.

BRIEF DESCRIPTION OF THE DRAWINGS

The foregoing summary, as well as the following detailed description may be better understood when read in conjunction with the accompanying drawings, which are incorporated in and form a part of the specification. The drawings serve to explain the principles of the invention and illustrate embodiments of the present invention that are preferred at the time the application was filed. It should be understood, however, that the invention is not limited to the precise arrangements and instrumentalities shown.

The accompanying drawings, which are incorporated in and form a part of the specification, illustrate the embodiments of the present invention and, together with the following description, serve to explain the principles of the invention. For the purpose of illustrating the invention, there are shown in the drawings embodiments which are presently preferred, it being understood, however, that the invention is not limited to the specific instrumentality or the precise arrangement of elements or process steps disclosed.

In the drawings:

In the drawings:

FIG. 10A is a perspective view of the testing, sample storage and screening apparatus of FIG. 1 showing a stopper and a stopper/swab.

FIG. 10B is an exploded view of the testing, sample storage and screening apparatus of FIG. 10A.

DETAILED DESCRIPTION OF THE PREFERRED EMBODIMENT

In describing a preferred embodiment of the invention, specific terminology will be selected for the sake of clarity. However, the invention is not intended to be limited to the specific terms so selected, and it is to be understood that each specific term includes all technical equivalents that operate in a similar manner to accomplish a similar purpose.

Preferred embodiments of the present invention will now be described in detail with reference to the accompanying drawings in which an apparatus for testing saliva in order to screen for drugs in accordance with the present invention is generally indicated at 10.

Figures 1, 2:
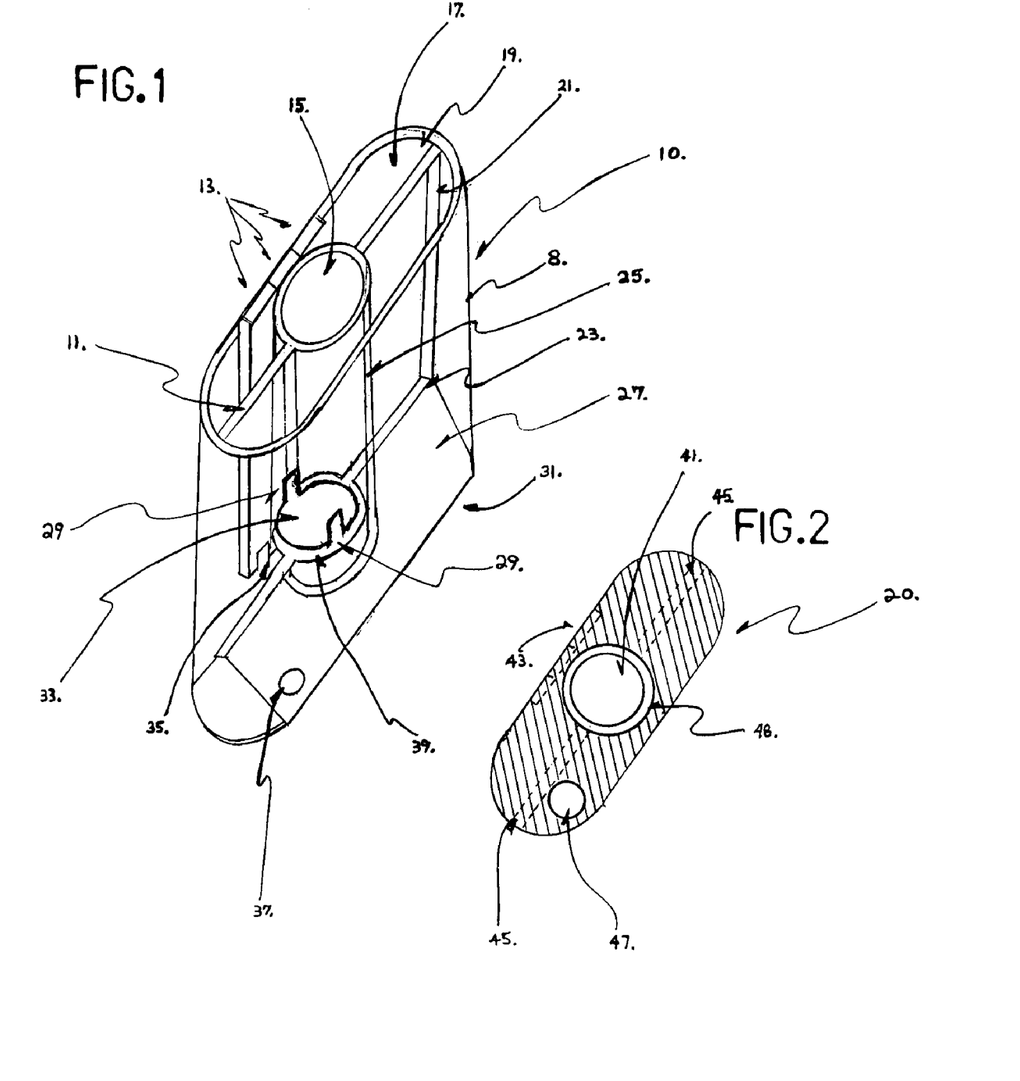
FIG. 1 is a partial top view of the self-contained, tamper-proof screening, testing and storage apparatus without the top cover and sample swab incorporated.
FIG. 2 is a top view of the top cover of the self-contained, tamper-proof screening, testing and storage apparatus shown in FIG. 1.

Referring now to FIG. 1, an apparatus 10 for screening for the presence of drugs in accordance with the present invention is shown. The apparatus 10 consists of a divided container 18 having exterior walls 26. The apparatus has a top end 98 and a bottom end 99. The divided container 18 has a tubular compartment 15 that is positioned proximately in the center of the divided container 18 and has divider walls 11 that extend radially outward from the tubular compartment 15 to the outer walls of the container. The divider walls 11 separate the apparatus 10 into two separate chambers, a first chamber 17 and a second chamber 21, respectively.

At the lower end of the hollow tubular compartment 15 there are two windows 29 that open into each of the divided chambers 17 and 21. Also, at the lower end of container 18 there is a bottom plug 30 that snaps into the bottom of container 18. The bottom plug 30 seals the entire lower end of the divided container and provides a seal between the divider walls 11 and bottom plug grooves 23. The bottom plug 30 also has a footer 33 that extends upward from bottom plug 30 into the lower end of the hollow section 15 of the container 18.

Referring now to FIGS. 10A and 10B, the footer 33 of the bottom plug 30 extends far enough into the tubular compartment 15 and has a diameter that provides a seal between the openings of the container with the bottom plug, although the footer does not provide a seal the entire length of the footer 33. The footer 33 does not extend upward far enough to seal the windows 29 that open onto the separate chambers 17 and 21. At the top of footer 29 the diameter is significantly small enough to prevent a seal between the footer 29 and the hollow interior of the tubular section 15. This area is referred to as the footer-locking bead 39.

The bottom plug also has tapered surfaces 27 (See FIG. 10B) on both sides for controlling the direction of the flow of the specimen within both chambers 17 and 21. The bottom plug also has a small reservoir 37 in chamber 21. This reservoir will be used to extract small amounts of specimen when and if a remote lab may need to access and remove a sample of the specimen. This will be better understood as we describe the other drawings in more detail.

In chamber 17 of apparatus 10 there are narrow sleeves 13 that extend from the top 98 of the container 18 to the bottom 99 of container 18. The sleeves 13 hold test strips. At the lower end of the divided container the sleeves 13 have small openings 35 that allow the test strips to be exposed to the sample.

Referring now to FIG. 2, the top view of the top cover 20 of the apparatus described in FIG. 1. The top cover 20 snaps and locks onto the divided container 18. The locking mechanism in FIG. 1, 19 provides a seal and locking means between the outer edge of the top cover 20 and the interior edge 19 of container 18. There are also sealing means (via friction fit) between the top cover 20 under surface and the container 18 described in FIG. 1.

In FIG. 1 the top surface of the divider wall 11 will be sealed with the under surface of the top cover 45. The top surface of the sleeves 13 of container 18 will be sealed with the under surface 43 of the top cover 20 and the top cover hollow center 41 will seal around the hollow section 15 of container 18 by the top cover seal 48.

The top cover 20 also has a small nipple 47 that extends upward so that it is perfectly aligned with the bottom plug reservoir 37 shown in FIGS. 1, 10A and 10B. The purpose will be understood later in this description.

Figure 3:
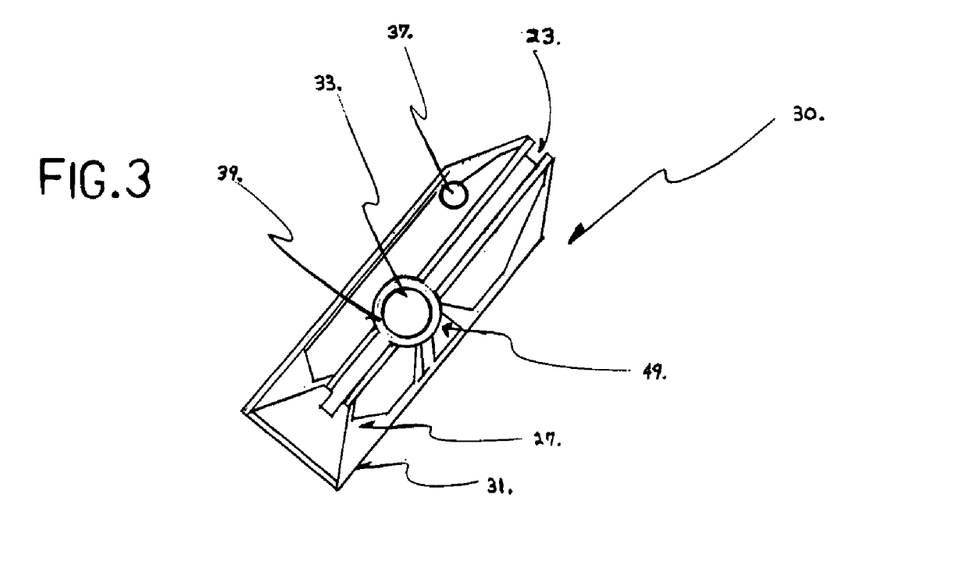
FIG. 3 is a partial top view of the bottom plug of the self-contained, tamper-proof screening, testing and storage apparatus shown in FIG. 1.

Referring now to FIG. 3, a partial top view of the bottom plug 30 of the apparatus described in FIG. 1. Bottom plug 30 seals the lower end of the divided container 18. Grooves 23 engage and seal the lower end of the divider walls 11 of container 18. The sealing and locking bead 31 of bottom plug 30 engages seals and locks onto to lower end of the divided container 18. The footer 33 of the bottom plug 30 engages and seals the lower section of the bottom plug 30. Note that the footer 33 does not entirely seal the windows 29 of the hollow section 15 of the divided container. Also, at the top of footer 33 the diameter is significantly small enough to prevent a seal between the footer 33 and the hollow interior of the tubular compartment 15. This area is referred to as the footer-locking bead 39. This footer-locking bead 39 will be described in FIG. 4. Bottom plug 30 has a reservoir 37 in chamber 21 of divided container 18. The reservoir 37 is aligned directly under the top cover 20 extended nipple 47. The extended nipple 47 described in FIG. 2 will provide tamper evident means to access the interior of chamber 21 for remote lab test verification purposes. Extended nipple 47 may be permanently cut off, thus providing access to chamber 21 of the divided container 18. Bottom plug 30 has small conduits 49 to control, focus and provide the maximum amount of sample to the openings 35 in the lower part of the sleeves 13 of container 18. This is especially important when there may be a small amount of a sample to be tested. Tapered walls 27 of the bottom plug 30 also control the flow of the sample specimen within both chambers 17 and 21 respectively.

Figure 4:
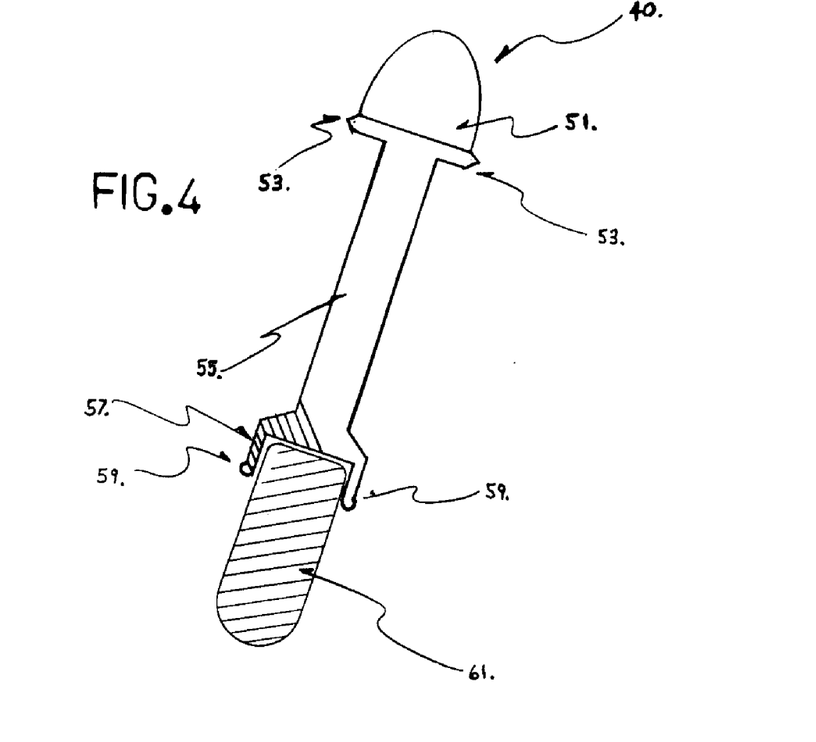
FIG. 4 is a perspective view of the sampling swab of the self-contained, tamper-proof screening, testing and storage apparatus shown in FIG. 1.

Referring now to FIG. 4, a perspective view of the specimen sample swab 40 for use with the apparatus described in FIG. 1. Swab 40 is comprised of a gripping area 51, a tamper proof lock 53 and a shaft 55. Swab 40 is used to extract a sample of saliva from one's mouth by placing the absorbent pad 61 into the mouth of the individual being tested. Swab 40 has a housing 57 that holds the absorbent pad 61 during use. Housing 57 has lock and seal means 59 that work I conjunction with the footer-locking bead 39 of bottom plug 30, previously described in the apparatus of FIG. 1.

Figure 5:
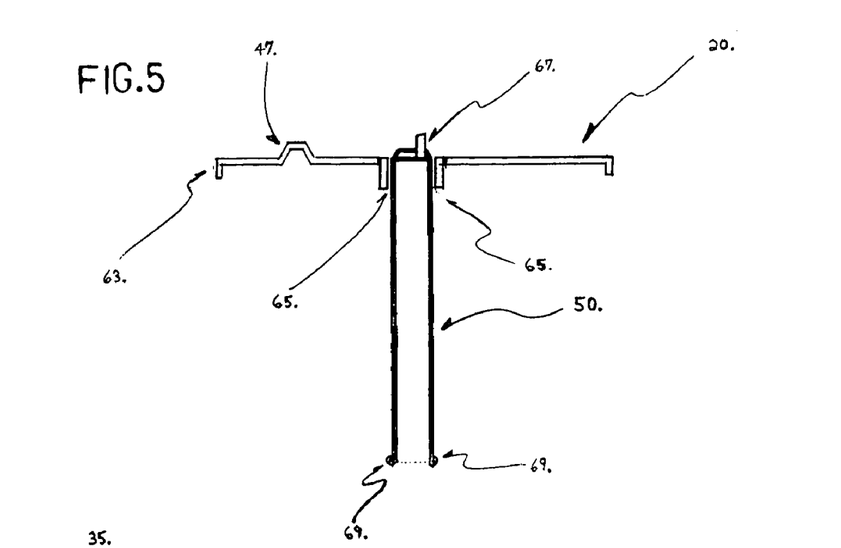
FIG. 5 is a cross sectional view of the top cover shown in FIG. 2 and the stopper for sealing the self-contained, tamper-proof screening, testing and storage apparatus shown in FIG. 1.

Referring now to FIG. 5, a cross-sectional view of the top cover shown in FIG. 2 and the stopper for sealing the self-contained, tamper-proof screening, testing and storage apparatus shown in FIG. 1. Stopper 50 has sealing means 69 that work in conjunction with the footer-locking bead 39 of bottom plug 30, previously described in the apparatus of FIG. 1. Note: The stopper seals the passage way windows 29 between the interior of hollow section 15 of divided container 18 and seals the footer-locking bead 39 of bottom plug 30, previously described in the apparatus of FIG. 1, although the stopper does not permanently lock in place. Stopper 50 is inserted through the top cover opening 41, prior to use. Stopper 50 incorporates pull-tab 67 that are used to remove stopper 50 from the apparatus 10.

Figure 6:
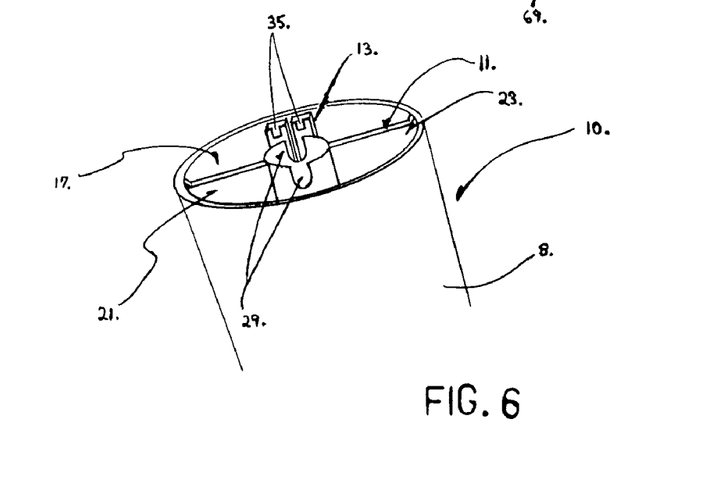
FIG. 6 is partial bottom view of the divided container that shows the hollow center section of the divided container and shows the sleeves that hold the test strips for the self-contained, tamper-proof screening, testing and storage apparatus shown in FIG. 1.

Referring now to FIG. 6, a partial bottom view of the divided container 18 that shows the hollow center section 15 of the divided container 18 and shows the sleeves 13 that hold the test strips for the self-contained, tamper-proof screening, testing and storage apparatus 10 shown in FIG. 1. (Although FIGS. 1 and 2 show three test-strip channels for holding test strips, FIG. 6 illustrates an embodiment with only two test-strip channels. A person skilled in the art, after reading this description, would understand that the number of test strip channels depends on the type of strips used and the number of tests/drugs for which the apparatus will be used.)

Figure 7:
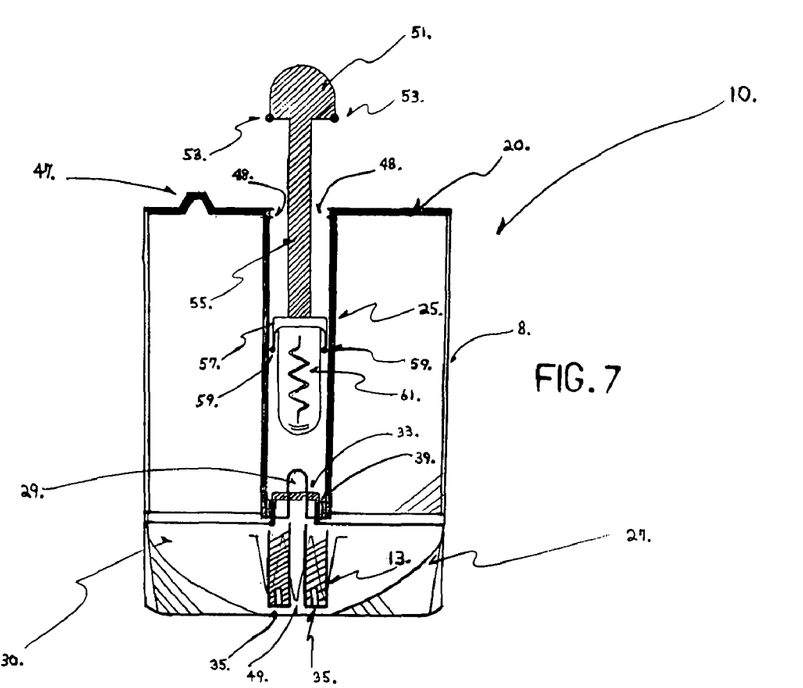
FIG. 7 is a perspective view of the self-contained, tamper-proof screening, testing and storage apparatus shown in FIG. 1 that also includes and incorporates the top cover and the sampling swab, respectively.

Referring now to FIG. 7, an apparatus 10 for screening for drugs is shown. Specific features of the subject apparatus 10 will become more apparent through the explanation of a screening for drug metabolites in a saliva sample. The test subject places specimen swab absorbent pad 61 into ones mouth for a short period of time. Absorbent pad 61 consists of a hydrophilic membrane, which enhances the collecting of a saliva specimen from the test subject. After the absorbent pad 61 is saturated with saliva the specimen swab 40 is pushed into the opening of the top cover 20 which is attached to the divided container 18 of apparatus 10. Eventually the bottom plug footer 33 will contact the absorbent pad 61 causing the absorbent pad 61 to compress, thus forcing the saliva specimen through both windows 29 which lead to both, chambers 17 and 21 (shown in FIG. 1) respectively. The housing 57 of specimen swab 40 prevents excess saliva from moving upward towards the specimen swab shaft 55. When the specimen swab 40 is fully compressed the locking bead 59 of housing 57 engages, locks and seals within the footer-looking bead 39 of the bottom plug 30. At this time the passage way between chambers 17 and 21 (shown in FIG. 1) are completely seal off from one another thus, the windows 29 of the divided container 18 are sealed off by housing 57 of the specimen swab 40 and the footer-locking bead 39 is sealed with the locking bead 59 of the specimen swab 40. Simultaneous, the specimen swab handle 51 engages and locks onto the top cover 20 by means, 48 of top cover and 53 of specimen swab handle thus, providing a permanent tamper proof lock and seal.

As the saliva specimen enters chambers 17 and 21 (shown in FIG. 1) the tapered walls 27 of bottom plug 30 control the flow of the specimen. Also, conduits 49 of bottom plug 30 provide a passageway directly towards the openings 35 in the test strip sleeves 13 of chamber 17 of the divided container 18 thus, maximizing the amount of specimen that can be used for activating the test strips. Saliva will also flow into chamber 21 which may mix with a preservative, if desired, or just remain isolated for purposes of future testing (confirmation) by a remote lab. If a test result is positive the entire apparatus 10 may be mailed to a remote laboratory for verification. The remote lab technician must cut off the extended nipple 47 of top cover 20 in order to access the stored unadulterated sample in chamber 21 of the divided container 18. Reservoir 37 of bottom plug 30 is positioned directly below extended nipple 47 of the top cover 20. A small sample may be removed with a pipette.

Figure 8:
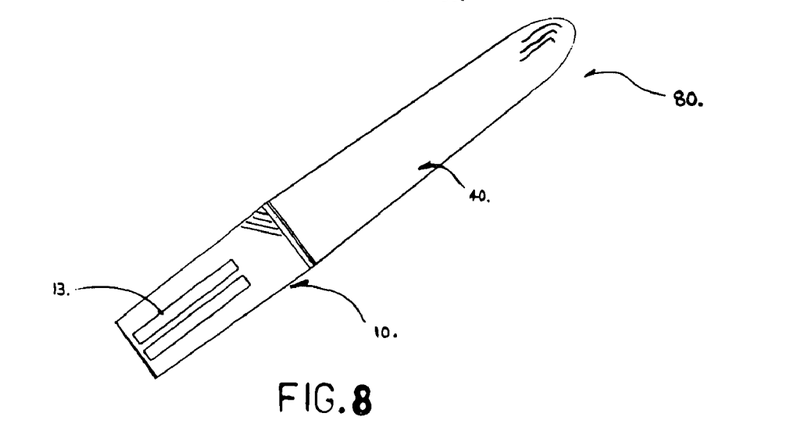
FIG. 8 represents an alternative shape/design of the self-contained, tamper-proof screening, testing and storage apparatus shown in FIG. 1 and FIG. 7.

Referring now to FIG. 8, an alternative shape/design of the self-contained, tamper-proof screening, testing and storage apparatus 10 shown in FIGS. 1 and 7. Apparatus 10 has a divided container 18, with test strip sleeves 13 and a specimen swab 40.

Figure 9:
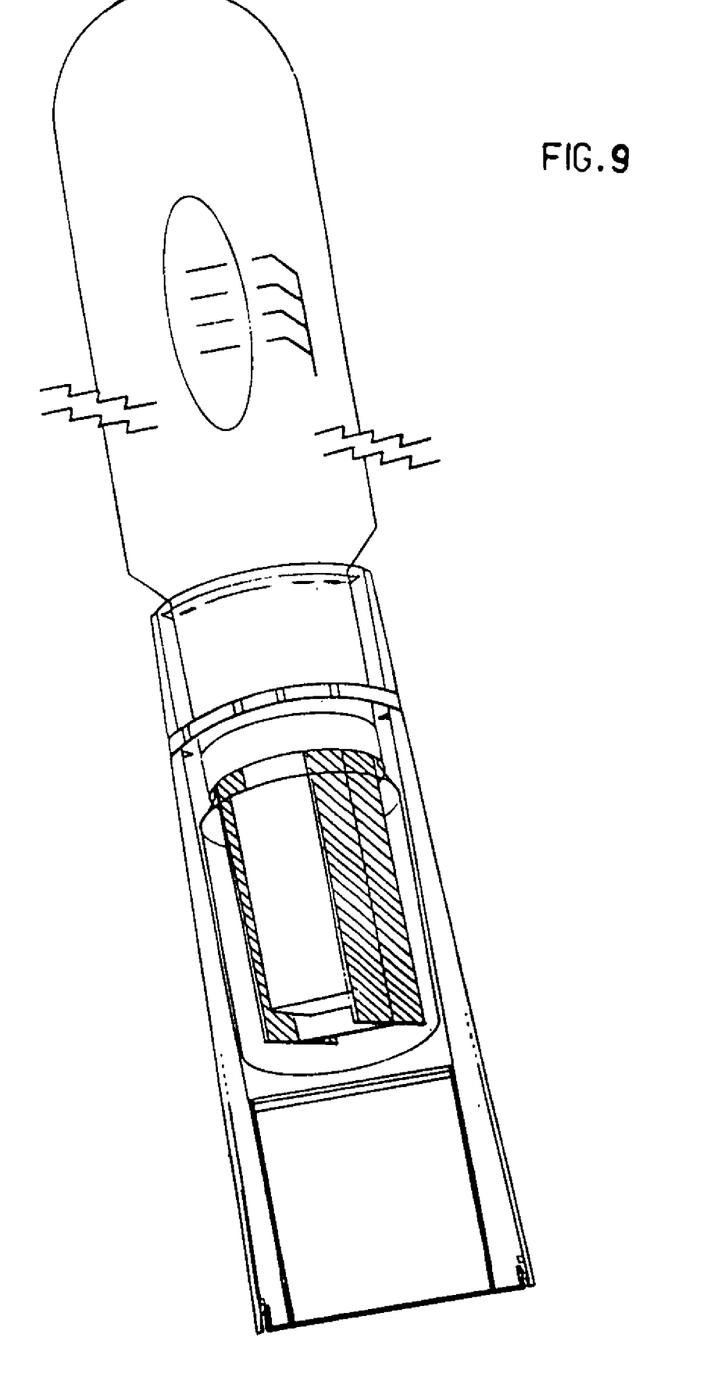
FIG. 9 is an exploded view of yet another embodiment of a testing, sample storage and screening apparatus.

Referring now to FIG. 9, an exploded view of yet another embodiment of a testing, sample storage and screening apparatus. Note: This embodiment incorporates both the test strips, the sleeves that hold the test strips and the absorbent pad within a single holder. The cover incorporates a flushing agent or preservative that is accessed when the cover is snapped onto the single holder.

Although this invention has been described and illustrated by reference to specific embodiments, it will be apparent to those skilled in the art that various changes and modifications may be made which clearly fall within the scope of this invention. The present invention is intended to be protected broadly within the spirit and scope of the appended claims.

I claim:

1. An apparatus for testing saliva comprising:
    a housing having a top end, a bottom end, a tubular compartment located proximate the middle of the housing, and first and second dividing walls in the interior of the apparatus that communicate with said tubular compartment for defining a first latitudinal compartment and a second latitudinal compartment, each latitudinal compartment spanning from the top end of the housing to the bottom end of the housing;
said tubular compartment having a first window that allows the interior of the tubular section to communicate with the interior of the first compartment and a second window that allows the interior of the tubular section to communicate with the interior of the second compartment, both windows positioned proximate the bottom of the tubular section;
    a bottom plug designed to seal the bottom end of the housing while keeping a distinct separation between said first compartment, said second compartment and said tubular compartment; the plug including a footer that sits directly beneath the tubular compartment; the bottom plug having a top surface with two tapered surfaces commencing at said dividing walls and tapering down towards the edge of the housing;
    a cap that releasably seals the top of said housing, the cap also designed to keep a distinct separation between said first compartment; said second compartment and said tubular compartment;
    a plurality of sleeves adapted to hold one or more test strips, the sleeves being positioned inside the interior of said first compartment, said sleeves including windows proximate the bottom of the apparatus for allowing at least a portion of said one or more test strips to be exposed to the interior of said first compartment; and
    an elongated swab having a gripping area at its first end connected to a stopper at its second end via a shaft, the stopper designed to hold an absorbent pad, the absorbent pad is designed to collect a sample;
    the elongated swab designed to be inserted into said tubular compartment of said housing;
said swab having a sealing member for permanently sealing the swab to the apparatus.

2. The apparatus of claim 1 wherein the absorbent pad is a hydrophillic foam.

3. The apparatus of claim 1 further comprising means for preserving saliva stored within said second latitudinal compartment.

4. The apparatus of claim 1 further comprising at least one or more test strips placed within one or more of said plurality of sleeves.

5. The apparatus of claim 4 wherein said test strips test for specific drugs and drug metabolites.

6. The apparatus of claim 1 further comprising a removable stopper that is placed within said tubular compartment for closing off both windows before a test is taken.

7. The apparatus of claim 1 further comprising a plug reservoir located on the half of the plug that projects into the second compartment, and a tamper-proof access port aligned directly over said reservoir.

8. The apparatus of claim 7 wherein said tamper-proof access port allows a pipette to break through and withdraw a sample from the reservoir.

9. The apparatus of claim 1 further comprising means to control the amount of sample discharge from the swab into each chamber.

10. The apparatus of claim 9 wherein said means to control the amount of liquid discharge comprises a patterned footer.

11. The apparatus of claim 10 wherein said patterned footer comprises a tapered top surface of said footer.

12. The apparatus of claim 10 wherein said patterned footer comprises grooves and other geometries to control the discharge of sample into each compartment.

13. The apparatus of claim 9 wherein said means to control the amount of liquid discharge comprises changing the size of one window opening into a compartment relative to the other window.

14. The apparatus of claim 1 wherein said stopper seals closed both windows thereby completely isolating two samples of saliva.

15. The apparatus of claim 14 wherein said swab further comprises a wiper to prevent specimen back-flow into the tubular compartment.

16. The apparatus of claim 14 wherein said swab further comprises a tamper-proof locking lip that secures the swab to the top cover, thereby locking the entire swab within the tubular compartment and simultaneously sealing said windows and isolating the samples.

17. The apparatus of claim 14 wherein said stopper comprises a locking means around its outer perimeter for permanently securing the swab within the tubular compartment and simultaneously sealing said windows and isolating the samples.

18. The apparatus of claim 1 wherein said housing is clear so that the samples within each compartment may be observed.

19. The apparatus of claim 1 wherein said housing proximate the plurality of sleeves is clear so that when said one or more test strips are inserted, and a test is taken, the said one or more test strips may be observed.

* * * * *